(12) United States Patent
Itagaki et al.

(10) Patent No.: US 7,705,165 B2
(45) Date of Patent: Apr. 27, 2010

(54) METHOD FOR PRODUCING OPTICALLY ACTIVE CYCLOPROPANECARBOXYLATE COMPOUND

(75) Inventors: Makoto Itagaki, Katano (JP); Ryo Minamida, Kyotanabe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 268 days.

(21) Appl. No.: 11/630,802

(22) PCT Filed: Jun. 30, 2005

(86) PCT No.: PCT/JP2005/012533

§ 371 (c)(1),
(2), (4) Date: Dec. 27, 2006

(87) PCT Pub. No.: WO2006/004180

PCT Pub. Date: Jan. 12, 2006

(65) Prior Publication Data

US 2008/0027235 A1    Jan. 31, 2008

(30) Foreign Application Priority Data

Jul. 1, 2004    (JP) .............................. 2004-195253

(51) Int. Cl.
*C07D 307/00* (2006.01)
*C07C 61/04* (2006.01)
(52) U.S. Cl. ...................................... 549/468; 562/506
(58) Field of Classification Search .................. 562/506
See application file for complete search history.

(56) References Cited

U.S. PATENT DOCUMENTS 6,858,559 B2    2/2005  Yamamoto et al.
2002/0177718 A1    11/2002  Yamamoto et al.

FOREIGN PATENT DOCUMENTS

EP    0 895 992 A2    2/1999

OTHER PUBLICATIONS

Bernardi, Luca, et al., "Catalytic Asymmetric Mannich Reactions of Glycine Derivatives with Imines. A New Approach to Optically Active α,β-Diamino Acid Derivatives", J. Org. Chem, 2003, vol. 68, pp. 2583-2591.
Denmark, Scott et al., "Effect of Ligand Structure in the Bisoxazoline Mediated Asymmetric Addition of Methyllithium to Imines", J. Org. Chem, 2000, vol. 65, pp. 5875-5878.
Evans, David A. et al., "An Improved Procedure for the Preparation of 2,2-Bis[2-[4(S)-tert-butyl-1,3-oxazolinyl]]propane [(S,S)-tert-Butylbis(oxazoline)] and Derived Copper (II) Complexes", J. Org. Chem, 1998, vol. 63, pp. 4541-4544.
Evans, David A. et al., "Chiral Bis(oxazoline)copper(II) Complexes as Lewis Acid Catalysts for the Enantioselective Diels—Alder Reaction", J. Am. Chem. Soc., 1999, vol. 121, pp. 7559-7573.

(Continued)

Primary Examiner—D. Margaret Seaman
Assistant Examiner—Nizal S Chandrakumar
(74) Attorney, Agent, or Firm—Foley & Lardner LLP

(57) ABSTRACT

A method for producing an optically active cyclopropanecarboxylate compound represented by the formula (5):

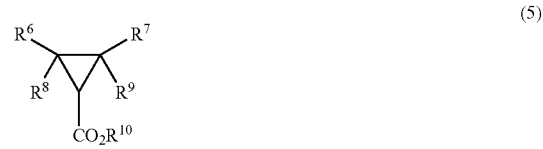

(5)

wherein $R^6$, $R^7$, $R^8$ and $R^9$ represent a C1-C6 alkyl group or the like and $R^{10}$ represents a C1-C6 alkyl group,
which comprises reacting an olefin represented by the formula (3):

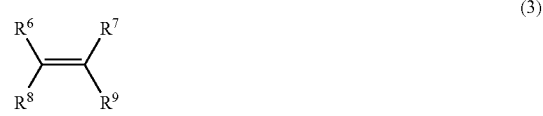

(3)

wherein $R^6$, $R^7$, $R^8$ and $R^9$ are as described above,
with a diazoacetic acid ester represented by the formula (4):

$N_2CHCO_2R^{10}$ (4)

wherein $R^{10}$ is as described above,
in the presence of an asymmetric copper complex obtained by mixing
  (A) at least one monovalent or divalent copper compound,
  (B) at least one optically active bisoxazoline compound represented by the formula (1):

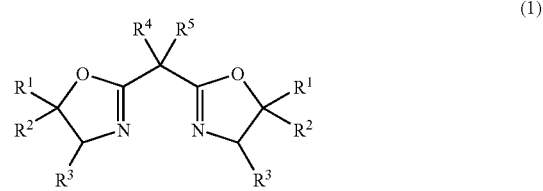

(1)

wherein $R^1$ and $R^2$ represent a C1-C6 alkyl group or the like; $R^3$ represents a tert-butyl group or the like; and $R^4$ and $R^5$ are the same and represent C1-C3 alkyl groups or the like, and
  (C) at least one fluorine compound represented by the formula (2):

$A\text{-}MF_6$ (2)

wherein A represents a trityl group or the like, and M represents a phosphorous atom or the like.

10 Claims, No Drawings

OTHER PUBLICATIONS

Lowenthal, Richard E. et al., "Asymmetric Copper-Catalyzed Cyclopropanation of Trisubstituted and Unsymmetrical cis-1,2-Disubstituted Olefins: Modified Bis-Oxazoline Ligands", Tetrahedron Letters, 1991, vol. 32, No. 50, pp. 7373-7376.

Østergaard, Niels et al., Scope and Limitations of Chiral bix(oxazoline) ligands in the Copper Catalysed Asymmetric Cyclopropanation of Trisubstituted Alkenes, Tetrahdedron Letters, 2001, vol. 57, pp. 6083-6088.

Simpson, James H. et al., "A Pilot-Scale Synthesis of (1R)-trans-2-(2,3-dihydro-4-benzofuranyl)cyclopropanecarboxylic acid: A Practical Application of Asymmetric Cyclopropanation using a Styrene as a Limiting Reagent", Tetrahedron, *Asymmetry*, vol. 14, 2003, pp. 3569-3574.

METHOD FOR PRODUCING OPTICALLY ACTIVE CYCLOPROPANECARBOXYLATE COMPOUND

TECHNICAL FIELD

The present invention relates to a method for producing an optically active cyclopropanecarboxylate compound.

BACKGROUND ART

Optically active cyclopropanecarboxylate compounds whose representative examples are (+)-trans-2,2-dimethyl-3-(2-methyl-1-propenyl)cyclopropanecarboxylate and (+)-trans-3,3-dimethyl-2-(acetoxymethyl)cyclopropanecarboxylate are important compounds as synthetic intermediates of pesticides and pharmaceuticals such as synthesized pyrethroid insecticides and methods for producing it are described in EP 895992 A, U.S. Pat. No. 6,858,559, Tetrahedron Lett., 32, 7373 (1991), Tetrahedron, 57, 6083 (2001) and the like.

DISCLOSURE OF THE INVENTION

The present invention provides a method for producing an optically active cyclopropanecarboxylate compound represented by the formula (5):

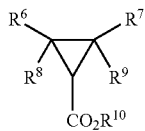

(5)

wherein $R^6$, $R^7$, $R^8$ and $R^9$ are the same or different, and independently represent a hydrogen atom; a halogen atom; a C1-C6 alkyl group which is optionally substituted with a halogen atom or atoms, a C1-C6 alkoxy group or groups, a C7-C12 aralkyloxy group or groups, a C2-C10 acyloxy group or groups, a C2-C7 alkoxycarbonyloxy group or groups, or a C7-C11 aryloxycarbonyloxy group or groups; a C1-C6 alkenyl group which is optionally substituted with a halogen atom or atoms or a C2-C7 alkoxycarbonyl group or groups; a C6-C10 aryl group which is optionally substituted with a C1-C6 alkoxy group or groups; a C7-C12 aralkyl group which is optionally substituted with a C1-C6 alkoxy group or groups; or a C2-C7 alkoxycarbonyl group which is optionally substituted with a halogen atom or atoms, a C1-C6 alkoxy group or groups, a C7-C12 aralkyloxy group or groups, a C2-C10 acyloxy group or groups, a C2-C7 alkoxycarbonyloxy group or groups, or a C7-C11 aryloxycarbonyloxy group or groups; provided that, when $R^6$ and $R^8$ represent the same, $R^6$ and $R^7$ represent different groups each other; and $R^{10}$ represents a C1-C6 alkyl group, which comprises reacting an olefin represented by the formula (3):

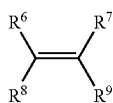

(3)

wherein $R^6$, $R^7$, $R^8$ and $R^9$ are as described above, with a diazoacetic acid ester represented by the formula (4)

$$N_2CHCO_2R^{10} \quad (4)$$

wherein $R^{10}$ is as described above, in the presence of an asymmetric copper complex obtained by mixing
(A) at least one monovalent or divalent copper compound,
(B) at least one optically active bisoxazoline compound represented by the formula (1):

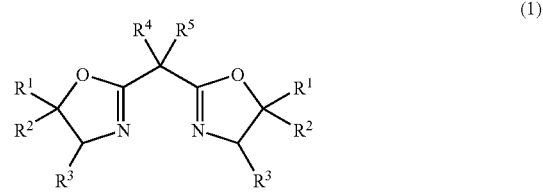

(1)

wherein $R^1$ and $R^2$ are the same or different, and independently represent a hydrogen atom; a C1-C6 alkyl group; a phenyl group which is optionally substituted with a C1-C6 alkyl group or groups or a C1-C6 alkoxy group or groups; or a C7-C12 aralkyl group which is optionally substituted with a C1-C6 alkoxy group or groups, or $R^1$ and $R^2$ are bonded together to represent a C2-C6 polymethylene group,
$R^3$ represents a methyl group; an isopropyl group; an isobutyl group; a tert-butyl group; a 1-naphthyl group; a 2-naphthyl group; a phenyl group which is optionally substituted with a C1-C6 alkyl group or groups or a C1-C6 alkoxy group or groups; or a C7-C12 aralkyl group which is optionally substituted with a C1-C6 alkoxy group or groups, and
$R^4$ and $R^5$ are the same and represent hydrogen atoms or C1-C3 alkyl groups, or $R^4$ and $R^5$ are bonded together to represent a C2-C5 polymethylene group, and
(C) at least one fluorine compound represented by the formula (2):

$$A\text{-}MF_6 \quad (2)$$

wherein A represents a lithium atom, a sodium atom, a potassium atom, a silver atom or a trityl group, and M represents a phosphorous, arsenic or antimony atom.

BEST MODE FOR CARRYING OUT THE PRESENT INVENTION

Examples of the monovalent or divalent copper compound which is component (A) include copper(I) trifluoromethanesulfonate, copper(I) acetate, copper(I) bromide, copper(I) chloride, copper(I) iodide, copper(I) hydroxide, copper(II) trifluoromethanesulfonate, copper(II) acetate, copper(II) bromide, copper(II) chloride, copper(II) iodide and copper(II) hydroxide and the monovalent copper compound is preferable. A copper halide such as copper(I) chloride, copper(I) bromide, copper(I) iodide, copper(II) chloride, copper(II) bromide and copper(II) iodide is preferable. These copper compounds may be used alone, or two or more kinds thereof may be used.

As the monovalent or divalent copper compound, a commercially available compound can be used as it is. A monovalent copper compound prepared by contacting the divalent copper compound with a reducing agent such as phenylhydrazine may be used. A monovalent copper compound may be generated to use by contacting the divalent copper compound with a reducing agent such as phenylhydrazine in the reaction system.

In the formula of the optically active bisoxazoline compound represented by the formula (1) (hereinafter, simply referred to as the optically active bisoxazoline compound (1)) which is the component (B), $R^1$ and $R^2$ are the same or different, and independently represent a hydrogen atom; a C1-C6 alkyl group; a phenyl group which is optionally substituted with a C1-C6 alkyl group or groups or a C1-C6 alkoxy group or groups; or a C7-C12 aralkyl group which is optionally substituted with a C1-C6 alkoxy group or groups, or $R^1$ and $R^2$ are bonded together to represent a C2-C6 polymethylene group.

Examples of the C1-C6 alkyl group include a straight or branched chain alkyl group such as a methyl, ethyl, n-propyl, isopropyl, n-butyl, isobutyl, n-pentyl, and n-hexyl group.

Examples of the C1-C6 alkoxy group include a straight or branched chain alkoxy group such as a methoxy, ethoxy, n-propoxy, isopropoxy, n-butoxy, isobutoxy, n-pentyloxy, and n-hexyloxy group.

Examples of the phenyl group which is optionally substituted with the C1-C6 alkyl group or groups or the C1-C6 alkoxy group or groups include a phenyl, 3-methylphenyl, 4-methylphenyl, 2-methoxyphenyl, 3-methoxyphenyl and 4-methoxyphenyl group.

Examples of the C7-C12 aralkyl group which is optionally substituted with the C1-C6 alkoxy group or groups include a benzyl, 2-methylbenzyl, 3-methylbenzyl, 4-methylbenzyl, (1-naphthyl)methyl, (2-naphthyl)methyl, 2-methoxybenzyl; 3-methoxylbenzyl and 4-methoxybenzyl group.

When $R^1$ and $R^2$ are bonded together to represent the C2-C6 polymethylene group, examples of the C2-C6 polymethylene group include an ethylene, trimethylene, tetramethylene, pentamethylene and hexamethylene group.

$R^3$ represents a methyl group; an isopropyl group; an isobutyl group; a tert-butyl group; a 1-naphthyl group; a 2-naphthyl group; a phenyl group which is optionally substituted with a C1-C6 alkyl group or groups or a C1-C6 alkoxy group or groups; or a C7-C12 aralkyl group which is optionally substituted with a C1-C6 alkoxy group or groups. Examples of the phenyl group which is optionally substituted with the C1-C6 alkyl group or groups or the C1-C6 alkoxy group or groups and the C7-C12 aralkyl group which may be substituted with the C1-C6 alkoxy group or groups include the same groups as those exemplified above.

$R^4$ and $R^5$ are the same and represent hydrogen atoms or C1-C3 alkyl groups, or $R^4$ and $R^5$ are bonded together to represent a C2-C5 polymethylene group.

Examples of the C1-C3 alkyl group include a methyl, ethyl, n-propyl and isopropyl group. When $R^4$ and $R^5$ are bonded together to represent the C2-C5 polymethylene group, examples of the C2-C5 polymethylene group include an ethylene, trimethylene, tetramethylene and pentamethylene group.

Examples of the optically active bisoxazoline compound (1) include bis[2-[(4S)-methyloxazoline]]methane, bis[2-[(4S)-methyl-5,5-dimethyloxazoline]]methane, bis[2-[(4S)-methyl-5,5-diethyloxazoline]]methane, bis[2-[(4S)-methyl-5,5-di(n-propyl)oxazoline]]methane, bis[2-[(4S)-methyl-5,5-diphenyloxazoline]]methane, bis[2-[(4S)-methyl-5,5-di(3-methylphenyl)oxazoline]]methane, bis[2-[(4S)-methyl-5,5-di(4-methylphenyl)oxazoline]]methane, bis[2-[(4S)-methyl-5,5-di(2-methoxyphenyl)oxazoline]]methane, bis[2-[(4S)-methyl-5,5-di(3-methoxyphenyl)oxazoline]]methane, bis[2-[(4S)-methyl-5,5-di(4-methoxyphenyl)oxazoline]]methane, bis[(4S)-methyl-5,5-dibenzyloxazoline]]methane, bis[2-[(4S)-methyl-5,5-di(3-methylbenzyl)oxazoline]]methane, bis[2-[(4S)-methyl-5,5-di(4-methylbenzyl)oxazoline]]methane, bis[2-[(4S)-methyl-5,5-di(2-methoxybenzyl)oxazoline]]methane, bis[2-[(4S)-methyl-5,5-di(3-methoxybenzyl)oxazoline]]methane, bis[2-[(4S)-methyl-5,5-di(4-methoxybenzyl)oxazoline]]methane, bis[2-[spiro[(4S)-methyloxazoline-5,1'-cyclobutane]]]methane, bis[2-[spiro[(4S)-methyloxazoline-5,1'-cyclopentane]]]methane, bis[2-[spiro[(4S)-methyloxazoline-5,1'-cyclohexane]]]methane, bis[2-[spiro[(4S)-methyloxazoline-5,1'-cycloheptane]]]methane, 2,2-bis[2-[(4S)-methyloxazoline]]propane, 2,2-bis[2-[(4S)-methyl-5,5-dimethyloxazoline]]propane, 2,2-bis[2-[(4S)-methyl-5,5-diethyloxazoline]]propane, 2,2-bis[2-[(4S)-methyl-5,5-di(n-propyl)oxazoline]]propane, 2,2-bis[2-[(4S)-methyl-5,5-diphenyloxazoline]]propane, 2,2-bis[2-[(4S)-methyl-5,5-di(3-methylphenyl)oxazoline]]propane, 2,2-bis[2-[(4S)-methyl-5,5-di(4-methylphenyl)oxazoline]]propane, 2,2-bis[2-[(4S)-methyl-5,5-di(2-methoxyphenyl)oxazoline]]propane, 2,2-bis[2-[(4S)-methyl-5,5-di(3-methoxyphenyl)oxazoline]]propane, 2,2-bis[2-[(4S)-methyl-5,5-di(4-methoxyphenyl)oxazoline]]propane, 2,2-bis[2-[(4S)-methyl-5,5-dibenzyloxazoline]]propane, 2,2-bis[2-[(4S)-methyl-5,5-di(3-methylbenzyl)oxazoline]]propane, 2,2-bis[2-[(4S)-methyl-5,5-di(4-methylbenzyl)oxazoline]]propane, 2,2-bis[2-[(4S)-methyl-5,5-di(2-methoxybenzyl)oxazoline]]propane, 2,2-bis[2-[(4S)-methyl-5,5-di(3-methoxybenzyl)oxazoline]]propane, 2,2-bis[2-[(4S)-methyl-5,5-di(4-methoxybenzyl)oxazoline]]propane, 2,2-bis[2-[spiro[(4S)-methyloxazoline-5,1'-cyclobutane]]]propane, 2,2-bis[2-[spiro[(4S)-methyloxazoline-5,1'-cyclopentane]]]propane, 2,2-bis[2-[spiro[(4S)-methyloxazoline-5,1'-cyclohexane]]]propane, 2,2-bis[2-[spiro[(4S)-methyloxazoline-5,1'-cycloheptane]]]propane, 3,3-bis[2-[(4S)-methyloxazoline]]pentane, 3,3-bis[2-[(4S)-methyl-5,5-dimethyloxazoline]]pentane, 3,3-bis[2-[(4S)-methyl-5,5-diethyloxazoline]]pentane, 3,3-bis[2-[(4S)-methyl-5,5-di(n-propyl)oxazoline]]pentane, 3,3-bis[2-[(4S)-methyl-5,5-diphenyloxazoline]]pentane, 3,3-bis[2-[(4S)-methyl-5,5-di(3-methylphenyl)oxazoline]]pentane, 3,3-bis[2-[(4S)-methyl-5,5-di(4-methylphenyl)oxazoline]]pentane, 3,3-bis[2-[(4S)-methyl-5,5-di(2-methoxyphenyl)oxazoline]]pentane, 3,3-bis[2-[(4S)-methyl-5,5-di(3-methoxyphenyl)oxazoline]]pentane, 3,3-bis[2-[(4S)-methyl-5,5-di(4-methoxyphenyl)oxazoline]]pentane, 3,3-bis[2-[(4S)-methyl-5,5-dibenzyloxazoline]]pentane, 3,3-bis[2-[(4S)-methyl-5,5-di(3-methylbenzyl)oxazoline]]pentane, 3,3-bis[2-[(4S)-methyl-5,5-di(4-methylbenzyl)oxazoline]]pentane, 3,3-bis[2-[(4S)-methyl-5,5-di(2-methoxybenzyl)oxazoline]]pentane, 3,3-bis[2-[(4S)-methyl-5,5-di(3-methoxybenzyl)oxazoline]]pentane, 3,3-bis[2-[(4S)-methyl-5,5-di(4-methoxybenzyl)oxazoline]]pentane, 3,3-bis[2-[spiro[(4S)-methyloxazoline-5,1'-cyclobutane]]]pentane, 3,3-bis[2-[spiro[(4S)-methyloxazoline-5,1'-cyclopentane]]]pentane, 3,3-bis[2-[spiro[(4S)-methyloxazoline-5,1'-cyclohexane]]]pentane, 3,3-bis[2-[spiro[(4S)-methyloxazoline-5,1'-cycloheptane]]]pentane, 4,4-bis[2-[(4S)-methyloxazoline]]heptane, 4,4-bis[2-[(4S)-methyl-5,5-dimethyloxazoline]]heptane, 4,4-bis[2-[(4S)-methyl-5,5-diethyloxazoline]]heptane, 4,4-bis[2-[(4S)-methyl-5,5-di(n-propyl)oxazoline]]heptane, 4,4-bis[2-[(4S)-methyl-5,5-diphenyloxazoline]]heptane, 4,4-bis[2-[(4S)-methyl-5,5-di(3-methylphenyl)oxazoline]]heptane, 4,4-bis[2-[(4S)-methyl-5,5-di(4-methylphenyl)oxazoline]]heptane, 4,4-bis[2-[(4S)-methyl-5,5-di(2-methoxyphenyl)oxazoline]]heptane, 4,4-bis[2-[(4S)-methyl-5,5-di(3-methoxyphenyl)oxazoline]]heptane, 4,4-bis[2-[(4S)-methyl-5,5-di(4-methoxyphenyl)oxazoline]]heptane, 4,4-bis[2-[(4S)-methyl-5,5-dibenzyloxazoline]]heptane, 4,4-bis[2-[(4S)-methyl-5,5-di(3-methylbenzyl)oxazoline]]heptane, 4,4-bis[2-[(4S)-methyl-5,5-di(4-methylbenzyl)oxazoline]]heptane, 4,4-bis[2-[(4S)-methyl-5,5-di(2-methoxybenzyl)oxazoline]]heptane, 4,4-bis[2-[(4S)-methyl-5,5-di(3-methoxybenzyl)oxazoline]]heptane, 4,4-bis[2-[(4S)-methyl-5,5-di(4-methoxybenzyl)oxazoline]] heptane, 4,4-bis[2-[spiro[(4S)-methyloxazoline-5,1'-cyclobutane]]]heptane, 4,4-bis[2-[spiro[(4S)-methyloxazoline-5,1'-cyclopentane]]]heptane, 4,4-bis[2-[spiro[(4S)-methyloxazoline-5,1'-cyclohexane]]]heptane, 4,4-bis[2-[spiro[(4S)-methyloxazoline-5,1'-cycloheptane]]]heptane, 1,1-bis[2-[(4S)-methyloxazoline]]cyclopropane, 1,1-bis[2-[(4S)-methyl-5,5-dimethyloxazoline]]cyclopropane, 1,1-bis[2-[(4S)-methyl-5,5-diethyloxazoline]]cyclopropane, 1,1-bis[2-[(4S)-methyl-5,5-di(n-propyl)oxazoline]]cyclopropane, 1,1-bis[2-[(4S)-methyl-5,5-diphenyloxazoline]]cyclopropane, 1,1-bis[2-[(4S)-methyl-5,5-di(3-methylphenyl)oxazoline]]cyclopropane, 1,1-bis[2-[(4S)-methyl-5,5-di(4-methylphenyl)oxazoline]] cyclopropane, 1,1-bis[2-[(4S)-methyl-5,5-dibenzyloxazoline]]cyclopropane, 1,1-bis[2-[(4S)-methyl-5,5-di(3-methylbenzyl)oxazoline]]cyclopropane, 1,1-bis[2-[(4S)-methyl-5,5-di(4-methylbenzyl)oxazoline]] cyclopropane, 1,1-bis[2-[(4S)-methyl-5,5-di(2-methoxybenzyl)oxazoline]]cyclopropane, 1,1-bis[2-[(4S)methyl-5,5-di(3-methoxybenzyl)oxazoline]]cyclopropane, 1,1-bis[2-[(4S)-methyl-5,5-di(4-methoxybenzyl)oxazoline]] cyclopropane, 1,1-bis[2-[spiro[(4S)-methyloxazoline-5,1'-cyclobutane]]]cyclopropane, 1,1-bis[2-[spiro[(4S)-methyloxazoline-5,1'-cyclopentane]]]cyclopropane, 1,1-bis[2-[spiro[(4S)-methyloxazoline-5,1'-cycloheptane]]]cyclopropane, 1,1-bis[2-[(4S)-methyloxazoline]]cyclobutane, 1,1-bis[2-[(4S)-methyl-5,5-dimethyloxazoline]]cyclobutane, 1,1-bis[2-[(4S)-methyl-5,5-diethyloxazoline]]cyclobutane, 1,1-bis[2-[(4S)-methyl-5,5-di(n-propyl)oxazoline]]cyclobutane, 1,1-bis[2-[(4S)-methyl-5,5-diphenyloxazoline]]cyclobutane, 1,1-bis[2-[(4S)-methyl-5,5-di(3-methylphenyl)oxazoline]] cyclobutane, 1,1-bis[2-[(4S)-methyl-5,5-di(4-methylphenyl)oxazoline]]cyclobutane, 1,1-bis[2-[(4S)-methyl-5,5-dibenzyloxazoline]]cyclobutane, 1,1-bis[2-[(4S)-methyl-5,5-di(3-methylbenzyl)oxazoline]]cyclobutane, 1,1-bis[2-[(4S)-methyl-5,5-di(4-methylbenzyl)oxazoline]] cyclobutane, 1,1-bis[2-[(4S)-methyl-5,5-di(2-methoxybenzyl)oxazoline]]cyclobutane, 1,1-bis[2-[(4S)-methyl-5,5-di(3-methoxybenzyl)oxazoline]]cyclobutane, 1,1-bis[2-[(4S)-methyl-5,5-di(4-methoxybenzyl)oxazoline]] cyclobutane, 1,1-bis[2-[spiro[(4S)-methyloxazoline-5,1'-cyclobutane]]]cyclobutane, 1,1-bis[2-[spiro[(4S)-methyloxazoline-5,1'-cyclopentane]]]cyclobutane, 1,1-bis[2-[spiro[(4S)-methyloxazoline-5,1'-cycloheptane]]]cyclobutane, 1,1-bis[2-[(4S)-methyloxazoline]]cyclopentane, 1,1-bis[2-[(4S)-methyl-5,5-dimethyloxazoline]]cyclopentane, 1,1-bis[2-[(4S)-methyl-5,5-diethyloxazoline]]cyclopentane, 1,1-bis[2-[(4S)-methyl-5,5-di(n-propyl)oxazoline]]cyclopentane, 1,1-bis[2-[(4S)-methyl-5,5-diphenyloxazoline]]cyclopentane, 1,1-bis[2-[(4S)-methyl-5,5-di(3-methylphenyl)oxazoline]]cyclopentane, 1,1-bis[2-[(4S)-methyl-5,5-di(4-methylphenyl)oxazoline]]cyclopentane, 1,1-bis[2-[(4S)-methyl-5,5-dibenzyloxazoline]]cyclopentane, 1,1-bis[2-[(4S)-methyl-5,5-di(3-methylbenzyl)oxazoline]]cyclopentane, 1,1-bis[2-[(4S)-methyl-5,5-di(4-methylbenzyl)oxazoline]]cyclopentane, 1,1-bis[2-[(4S)-methyl-5,5-di(2-methoxybenzyl)oxazoline]]cyclopentane, 1,1-bis[2-[(4S)-methyl-5,5-di(3-methoxybenzyl)oxazoline]]cyclopentane, 1,1-bis[2-[(4S)-methyl-5,5-di(4-methoxybenzyl)oxazoline]]cyclopentane, 1,1-bis[2-[spiro[(4S)-methyloxazoline-5,1'-cyclobutane]]]cyclopentane, 1,1-bis[2-[spiro[(4S)-methyloxazoline-5,1'-cyclopentane]]]cyclopentane, 1,1-bis[2-[spiro[(4S)-methyloxazoline-5,1'-cycloheptane]]] cyclopentane, 1,1-bis[2-[(4S)-methyloxazoline]] cyclohexane, 1,1-bis[2-[(4S)-methyl-5,5-dimethyloxazoline]]cyclohexane, 1,1-bis[2-[(4S)-methyl-5,5-diethyloxazoline]]cyclohexane, 1,1-bis[2-[(4S)-methyl-5,5-di(n-propyl)oxazoline]]cyclohexane, 1,1-bis[2-[(4S)-methyl-5,5-diphenyloxazoline]]cyclohexane, 1,1-bis[2-[(4S)-methyl-5,5-di(3-methylphenyl)oxazoline]] cyclohexane, 1,1-bis[2-[(4S)-methyl-5,5-di(4-methylphenyl)oxazoline]]cyclohexane, 1,1-bis[2-[(4S)-methyl-5,5-dibenzyloxazoline]]cyclohexane, 1,1-bis[2-[(4S)-methyl-5,5-di(3-methylbenzyl)oxazoline]] cyclohexane, 1,1-bis[2-[(4S)-methyl-5,5-di(4-methylbenzyl)oxazoline]]cyclohexane, 1,1-bis[2-[(4S)-methyl-5,5-di(2-methoxybenzyl)oxazoline]]cyclohexane, 1,1-bis[2-[(4S)-methyl-5,5-di(3-methoxybenzyl)oxazoline]] cyclohexane, 1,1-bis[2-[(4S)-methyl-5,5-di(4-methoxybenzyl)oxazoline]]cyclohexane, 1,1-bis[2-[spiro[(4S)-methyloxazoline-5,1'-cyclobutane]]]cyclohexane, 1,1-bis[2-[spiro[(4S)-methyloxazoline-5,1'-cyclopentane]]]cyclohexane, 1,1-bis[2-[spiro[(4S)-methyloxazoline-5,1'-cycloheptane]]] cyclohexane; and these compounds in which methyl group at the 4-position of the oxazoline ring is respectively replaced with an isopropyl, isobutyl, tert-butyl, benzyl, phenyl, 1-naphthyl or 2-naphthyl group. These compounds of which the configuration (4S) at the 4-position of the oxazoline ring is changed to (4R) such as bis[2-[(4R)-methyloxazoline]] methane are also exemplified.

Further, these compounds of which one configuration is (4S) and other is (4R) among two bisoxazoline skeletons such as 1-[2-[(4R)-methyloxazoline]-1-[2-[(4S)-methyloxazoline]]methane are also exemplified.

These optically active bisoxazoline compounds (1) may be used alone, or two or more kinds thereof may be used.

The optically active bisoxazoline compound (1) can be produced by a method comprising contacting an optically active diamide compound represented by the formula (8):

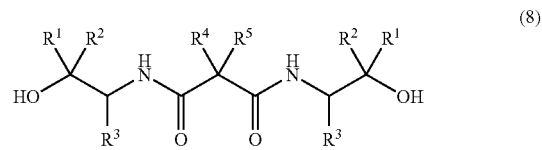

(8)

wherein $R^1$, $R^2$, $R^3$, $R^4$ and $R^5$ are the same as described above, which is obtained by reacting an optically active aminoalcohol compound represented by the formula (6):

(6)

wherein R¹, R², and R³ are the same as described above, with a compound represented by the formula (7):

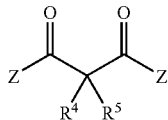

wherein R⁴ and R⁵ are the same as described above and Z represents an alkoxy group or a halogen atom, with a Lewis acid, for example, as described in EP 895992 A.

In the formula of the fluorine compound represented by the formula (2) (hereinafter, simply referred to as the fluorine compound (2)) which is the component (C), A represents a lithium atom, a sodium atom, a potassium atom, a silver atom or a trityl group and the trityl group is preferable. M represents a phosphorous, arsenic or antimony atom, and the phosphorous atom or the antimony atom is preferable.

Examples of the fluorine compound (2) include lithium hexafluorophosphate, sodium hexafluorophosphate, potassium hexafluorophosphate, silver hexafluorophosphate, trityl hexafluorophosphate, lithium hexafluoroarsenate, sodium hexafluoroarsenate, potassium hexafluoroarsenate, silver hexafluoroarsenate, trityl hexafluoroarsenate, sodium hexafluoroantimonate, potassium hexafluoroantimonate, silver hexafluoroantimonate and trityl hexafluoroantimonate. In terms of handling easily, trityl hexafluorophosphate and trityl hexafluoroantimonate are preferable. The fluorine compound (2) may be used alone, or two or more kinds thereof may be used.

As the fluorine compound (2), a commercial available compound can be used as it is.

The amount of the component (B) to be used is usually 0.8 to 5 moles, preferable 0.9 to 2 moles relative to 1 mole of the component (A).

The amount of the component (C) to be used is usually 0.8 to 5 moles, preferable 0.9 to 2 moles relative to 1 mole of the component (A).

The asymmetric copper complex of the present invention can be obtained by mixing the component (A), the component (B) and the component (C). The mixing order is not particularly limited and for example, it is carried out by a method comprising mixing the component (A) and the component (B) in a solvent followed by adding the component (C) thereto and the like.

The operation of mixing is usually carried out in the presence of a solvent. Examples of the solvent include a halogenated hydrocarbon solvent such as dichloromethane, 1,2-dichloroethane, chloroform and carbon tetrachloride, an aromatic hydrocarbon solvent such as toluene and xylene, and an ester solvent such as ethyl acetate. When the olefin represented by the formula (3) (hereinafter, simply referred to as the olefin (3)) described below is a liquid, the olefin (3) may be used as the solvent. The amount of the solvent to be used is usually 10 to 500 parts by weight relative to 1 part by weight of the component (A).

The operation of mixing is usually carried out in an atmosphere of an inert gas such as argon and nitrogen. The temperature of mixing is usually −20 to 100° C.

The asymmetric copper complex can be isolated by concentrating a solution obtained by mixing the component (A), the component (B) and the component (C), and the solution obtained may be used for the reaction of the olefin (3) and the diazoacetic acid ester represented by the formula (4) (hereinafter, simply referred to as the diazoacetic acid ester (4)) described below without isolating the asymmetric copper complex.

The optically active cyclopropanecarboxylate compound represented by the formula (5) (hereinafter, simply referred to as the optically active cyclopropane compound (5)) is obtained by reacting the olefin (3) with the diazoacetic acid ester (4) in the presence of the asymmetric copper complex thus obtained.

In the formula of the olefin (3), $R^6$, $R^7$, $R^8$ and $R^9$ are the same or different, and independently represent a hydrogen atom; a halogen atom; a C1-C6 alkyl group which is optionally substituted with a halogen atom or atoms, a C1-C6 alkoxy group or groups, a C7-C12 aralkyloxy group or groups, a C2-C10 acyloxy group or groups, a C2-C7 alkoxycarbonyloxy group or groups, or a C7-C11 aryloxycarbonyloxy group or groups; a C1-C6 alkenyl group which is optionally substituted with a halogen atom or atoms or a C2-C7 alkoxycarbonyl group or groups; a C6-C10 aryl group which is optionally substituted with a C1-C6 alkoxy group or groups; a C7-C12 aralkyl group which is optionally substituted with a C1-C6 alkoxy group or groups; or a C2-C7 alkoxycarbonyl group which is optionally substituted with a halogen atom or atoms, a C1-C6 alkoxy group or groups, a C7-C12 aralkyloxy group or groups, a C2-C10 acyloxy group or groups, a C2-C7 alkoxycarbonyloxy group or groups, or a C7-C11 aryloxycarbonyloxy group or groups.

Examples of 7 the halogen atom include a fluorine, chlorine, bromine and iodine atom.

Examples of the halogen atom and the C1-C6 alkoxy group of the C1-C6 alkyl group which is optionally substituted with the halogen atom or atoms, the C1-C6 alkoxy group or groups, the C7-C12 aralkyloxy group or groups, the C2-C10 acyloxy group or groups, the C2-C7 alkoxycarbonyloxy group or groups, or the C7-C11 aryloxycarbonyloxy group or groups are the same as those exemplified above. Examples of the C7-C12 aralkyloxy group include a benzyloxy, 4-methylbenzyloxy and (1-naphthyl)methoxy group. Examples of the C2-C10 acyloxy group include an acetoxy and benzoyloxy group. Examples of the C2-C7 alkoxycarbonyloxy group include a methoxycarbonyloxy, ethoxycarbonyloxy and tert-butoxycarbonyloxy group. Examples of the C7-C11 aryloxycarbonyloxy group include a phenoxycarbonyloxy group.

Examples of the C1-C6 alkyl group which is optionally substituted with the halogen atom or atoms, the C1-C6 alkoxy group or groups, the C7-C12 aralkyloxy group or groups, the C2-C10 acyloxy group or groups, the C2-C7 alkoxycarbonyloxy group or groups, or the C7-C11 aryloxycarbonyloxy group or groups include a methyl, ethyl, n-propyl, isopropyl, n-butyl, isobutyl, n-pentyl, chloromethyl, fluoromethyl, trifluoromethyl, chloroethyl, methoxymethyl, ethoxymethyl, n-propoxymethyl, isopropoxymethyl, n-butoxymethyl, tert-butoxymethyl, benzyloxymethyl, acetoxymethyl, benzoylmoxymethyl, methoxycarbonyloxymethyl, ethoxycarbonyloxymethyl, tert-butoxycarbonyloxymethyl and phenoxycarbonyloxymethyl group.

Examples of the C1-C6 alkenyl group which is optionally substituted with the halogen atom or atoms or the C2-C7 alkoxycarbonyl group or groups include an ethenyl, 1-propenyl, 2-propenyl, 2-methyl-propenyl, 1-butenyl, 2-butenyl, 3-butenyl, 1-chloro-2-propenyl and 2-methoxycarbonyl-1-propenyl group.

Examples of the C6-C10 aryl group which is optionally substituted with the C1-C6 alkoxy group or groups include a phenyl, 1-naphthyl, 2-naphthyl, 2-methylphenyl, 4-methylphenyl, 3-(methoxymethyl)phenyl and 2,3-dihydrobenzofuran-4-yl group.

Examples of the C7-C12 aralkyl group which is optionally substituted with the C1-C6 alkoxy group or groups include a benzyl, 2-methylbenzyl, 3-methylbenzyl, 4-methylbenzyl, 2-methoxybenzyl, 3-methoxybenzyl, 4-methoxybenzyl, (1-naphthyl)methyl and (2-naphthyl)methyl group.

Examples of the C2-C7 alkoxycarbonyl group which is optionally substituted with the halogen atom or atoms, the C1-C6 alkoxy group or groups, the C7-C12 aralkyloxy group or groups, the C2-C10 acyloxy group or groups, the C2-C7 alkoxycarbonyloxy group or groups, or the C7-C11 aryloxycarbonyloxy group or groups include a methoxycarbonyl, ethoxycarbonyl, n-propoxycarbonyl, isopropoxycarbonyl, n-butoxycarbonyl, isobutoxycarbonyl and n-pentyloxycarbonyl group.

When $R^6$ and $R^8$ represent the same in the formula of the olefin (3), $R^6$ and $R^7$ represent different groups each other.

Examples of the olefin (3) include propene, fluoroethylene, 1-fluoro-1-chloroethylene, 1-butene, isobutene, 1-pentene, 1-hexene, 1-octene, 4-chloro-1-butene, 2-pentene, 2-heptene, 2-methyl-2-butene, 2,5-dimethyl-2,4-hexadiene, 2-chloro-5-methyl-2,4-hexadiene, 2-fluoro-5-methyl-2,4-hexadiene, 1,1,1-trifluoro-5-methyl-2,4-hexadiene, 2-methoxycarbonyl-5-methyl-2,4-hexadiene, 1,1-difluoro-4-methyl-1,3-pentadiene, 1,1-dichloro-4-methyl-1,3-pentadiene, 1,1-dibromo-4-methyl-1,3-pentadiene, 1-chloro-1-fluoro-4-methyl-1,3-pentadiene, 1-fluoro-1-bromo-4-methyl-1,3-pentadiene, 2-methyl-2,4-hexadiene, 1-fluoro-1,1-dichloro-4-methyl-2-pentene, 1,1,1-trichloro-4-methyl-3-pentene, 1,1,1-tribromo-4-methyl-3-pentene, 2,3-dimethyl-2-pentene, 2-methyl-3-phenyl-2-butene, 2-bromo-2,5-dimethyl-4-hexene, 2-chloro-2,5-dimethyl-4-hexene, 1-chloro-2,5-dimethyl-2,4-hexadiene, (3-methyl-2-butenyl)methyl ether, (3-methyl-2-butenyl)tert-butyl ether, (3-methyl-2-butenyl)benzyl ether, 3-methyl-2-butenyl acetate, 3-methyl-2-butenyl benzoate, (3-methyl-2-butenyl)methyl carbonate, (3-methyl-2-butenyl)tert-butyl carbonate, (3-methyl-2-butenyl)phenyl carbonate, styrene and 4-vinyl-2,3-dihydrobenzofuran.

In the formula of the diazoacetic acid ester (4), $R^{10}$ represents a C1-C6 alkyl group. Examples of the alkyl group include a straight chain or branched chain alkyl group such a methyl, ethyl, n-propyl, isopropyl, n-butyl, isobutyl and n-pentyl group. Examples of the diazoacetic acid ester (4) include methyl diazoacetate, ethyl diazoacetate, n-propyl diazoacetate, isopropyl diazoacetate, n-butyl diazoacetate, isobutyl diazoacetate and tert-butyl diazoacetate.

As the diazoacetic acid ester (4), those produced by a known method such as Organic Synthesis Collective Volume 3, p. 392 can be used.

The amount of the asymmetric copper complex to be used is usually 0.00001 to 0.5 mole, preferably in the range of about 0.0001 to 0.05 mole in terms of the copper metal relative to 1 mole of the diazoacetic acid ester (4).

The amount of the olefin (3) to be used is usually 1 mole or more, preferably 1.2 moles or more relative to 1 mole of the diazoacetic acid ester (4). There is no specific upper limit and, when the olefin (3) is a liquid, excess amount thereof, for example, about 100 moles relative 1 mole of the diazoacetic acid ester (4), may be used as the solvent.

The reaction of the olefin (3) and the diazoacetic acid ester (4) is usually carried out in an atmosphere of an inert gas such as argon and nitrogen. Since water adversely affects the reaction, the reaction is preferably carried out with suppressing the amount of water present in the reaction system. As a method for suppressing the amount of water present in the reaction system, method comprising making a dehydrating agent such as molecular sieves, magnesium sulfate and sodium sulfate anhydride coexist in the reaction system, and using the olefin (3) or the solvent previously subjected to dehydration treatment.

The reaction temperature is usually about −50 to 150° C., preferably about −20 to 80° C.

The reaction of the olefin (3) and the diazoacetic acid ester (4) is usually carried out by mixing the asymmetric copper complex, the olefin (3) and the diazoacetic acid ester (4), and if necessary, in the presence of a solvent. The mixing order is not particularly limited. Usually, the asymmetric copper complex and the olefin (3) are mixed in the solvent and then the diazoacetic acid ester (4) is added thereto.

Examples of the solvent include a halogenated hydrocarbon solvent such as dichloromethane, 1,2-dichloroethane, chloroform and carbon tetrachloride, an aliphatic hydrocarbon solvent such as hexane, heptane and cyclohexane, an aromatic hydrocarbon solvent such as toluene and xylene, and an ester solvent such as ethyl acetate. They can be used alone or in the form of a mixed solvent. As described above, when the olefin (3) is a liquid, the olefin (3) may also be used as the solvent. When the solvent is used, the amount of the solvent to be used is not particularly limited, and in viewpoint of the volume efficiency and the properties of the reaction mixture, the amount thereof is usually about 2 to 30 parts by weight, preferably about 4 to 20 parts by weight relative to 1 part by weight of the diazoacetic acid ester (4).

When the asymmetric copper complex prepared using the divalent copper compound as the component (A) is used, a reducing agent such as phenylhydrazine may be used together.

After completion of the reaction, the optically active cyclopropane compound (5) can be isolated by, for example, distilling the reaction mixture. The optically active cyclopropane compound (5) isolated may be further purified, if necessary, by a conventional purification means such as column chromatography.

Examples of the optically active cyclopropane compound (5) include optically active methyl 2-fluorocyclopropanecarboxylate, optically active methyl 2-fluoro-2-chlorocyclopropanecarboxylate, optically active methyl 2-methylcyclopropanecarboxylate, optically active methyl 2,2-dimethylcyclopropanecarboxylate, optically active methyl 2,2-dimethyl-3-(2-methyl-1-propenyl)cyclopropanecarboxylate, optically active methyl 2,2-dimethyl-3-(2,2-dichloroethenyl)cyclopropanecarboxylate, optically active methyl 2,2-dimethyl-3-(2,2,2-trichloroethyl)cyclopropanecarboxylate, optically active methyl 2,2-dimethyl-3-(2,2,2-tribromoethyl)cyclopropanecarboxylate, optically active methyl 2,2-dimethyl-3-(2,2-dibromoethenyl)cyclopropanecarboxylate, optically active methyl 2,2-dimethyl-3-(2,2-difluoroethenyl)cyclopropanecarboxylate, optically active methyl 2,2-dimethyl-3-(2-fluoro-2-chloroethenyl)cyclopropanecarboxylate, optically active methyl 2,2-dimethyl-3-(2-fluoro-2-bromoethenyl)cyclopropanecarboxylate, optically active methyl 2,2-dimethyl-3-(2-fluoro-1-propenyl)cyclopropanecarboxylate, optically active methyl 2,2-dimethyl-3-(2-chloro-1-propenyl)cyclopropanecarboxylate, optically active methyl 2,2-dimethyl-3-(2-chloro-2-trifluoromethylethenyl)cyclopropanecarboxylate, optically active methyl 2,2-dimethyl-3-(2-methoxycarbonyl-1-propenyl)cyclopropanecarboxylate, optically active methyl 2,2-dimethyl-3-(2-chloro-2-methylpropyl)cyclopropanecarboxylate, optically active methyl 2,2-dimethyl-3-(2-bromo-2-methylpropyl)cyclopropanecarboxylate, optically active methyl 2,2-dimethyl-3-(1-propenyl)cyclopropanecarboxylate, optically active methyl 3,3- dimethyl-2-(methoxymethyl)cyclopropanecarboxylate, optically active methyl 3,3-dimethyl-2-(tert-butoxymethyl)cyclopropanecarboxylate, optically active methyl 3,3-dimethyl-2-(benzyloxymethyl)cyclopropanecarboxylate, optically active methyl 3,3-dimethyl-2-(acetoxymethyl)cyclopropanecarboxylate, optically active methyl 3,3-dimethyl-2-(benzoyloxymethyl)cyclopropanecarboxylate, optically active methyl 3,3-dimethyl-2-(methoxycarbonyloxymethyl)cyclopropanecarboxylate, optically active methyl 3,3-dimethyl-2-(tert-butoxycarbonyloxymethyl)cyclopropanecarboxylate, optically active methyl 3,3-dimethyl-2-(phenoxycarbonyloxymethyl)cyclopropanecarboxylate, optically active methyl 2-phenylcyclopropanecarboxylate and optically active methyl 2-(2,3-dihydrobenzofuran-4-yl)cyclopropanecarboxylate; and compounds wherein the above methyl ester moieties are replaced with ethyl, n-propyl, isopropyl, isobutyl or tert-butyl ester moieties.

EXAMPLES

In the following Examples, the yield was calculated based on the diazoacetic acid ester by the gas chromatography internal standard method. The trans-isomer/cis-isomer ratio was calculated based on the area ratio of the gas chromatography. The optically purity was calculated based on the area ratio of the liquid chromatography. In Examples 1 to 5 and Comparative Examples 1 to 2, the trans-isomer means the compound having the ester group at 1-position and the substituent at 2-position on the opposite side with respect to the cyclopropane ring plane and the cis-isomer means the compound having the ester group at 1-position and the substituent at 2-position on the same side. In Examples 6 to 7 and Comparative Example 3, the trans-isomer means the compound having the ester group at 1-position and the substituent at 3-position on the opposite side with respect to the cyclopropane ring plane and the cis-isomer means the compound having the ester group at 1-position and the substituent at 3-position on the same side.

Example 1

Into a 50 ml Schlenk tube purged with nitrogen, 1.98 mg of copper(I) chloride, 6.43 mg of 1,1-bis[2-[(4S)-(tert-butyl)oxazoline]]cyclopropane and 5 ml of 1,2-dichloroethane were charged. To the pale yellow mixture obtained by mixing them, 5.56 mg of silver hexafluorophosphate was added and the resulting mixture was stirred at room temperature for 10 minutes to obtain the lime green solution containing the asymmetric copper complex. In the solution, silver chloride was precipitated. After 7.69 g of 3-methyl-2-butenyl acetate was added to the solution and the inner temperature was adjusted to 20° C., 5 ml of the 1,2-dichloroethane solution containing ethyl diazoacetate (concentration: 4 mol/l) was added dropwise thereto over 4 hours and the resulting mixture was reacted at the same temperature for 30 minutes to obtain the solution containing ethyl 3,3-dimethyl-2-(acetoxymethyl)cyclopropanecarboxylate.
Yield: 69%
Trans-isomer/cis-isomer ratio: 84/16
Optically purity: trans-isomer 92% e.e. ((+)-isomer), cis-isomer 55% e.e. ((+)-isomer)

Example 2

Into a 50 ml Schlenk tube purged with nitrogen, 1.98 mg of copper(I) chloride, 6.43 mg of 1,1-bis[2-[(4S)-(tert-butyl)oxazoline]]cyclopropane and 5 ml of 1,2-dichloroethane were charged. To the pale yellow mixture obtained by mixing them, 7.56 mg of silver hexafluoroantimonate was added and the resulting mixture was stirred at room temperature for 10 minutes to obtain the lime green solution containing the asymmetric copper complex. In the solution, silver chloride was precipitated. After 7.69 g of 3-methyl-2-butenyl acetate was added to the solution and the inner temperature was adjusted to 20° C., 5 ml of the 1,2-dichloroethane solution containing ethyl diazoacetate (concentration: 4 mol/l) was added dropwise thereto over 4 hours and the resulting mixture was reacted at the same temperature for 30 minutes to obtain the solution containing ethyl 3,3-dimethyl-2-(acetoxymethyl)cyclopropanecarboxylate.
Yield: 69%
Trans-isomer/cis-isomer ratio: 84/16
Optically purity: trans-isomer 92% e.e. ((+)-isomer), cis-isomer 36% e.e. ((+)-isomer)

Example 3

Into a 50 ml Schlenk tube purged with nitrogen, 1.98 mg of copper(I) chloride, 6.43 mg of 1,1-bis[2-[(4S)-(tert-butyl)oxazoline]]cyclopropane and 5 ml of 1,2-dichloroethane were charged. To the pale yellow mixture obtained by mixing them, 3.34 mg of lithium hexafluorophosphate was added and the resulting mixture was stirred at room temperature for 10 minutes to obtain the lime green solution containing the asymmetric copper complex. In the solution, lithium chloride was precipitated. After 7.69 g of 3-methyl-2-butenyl acetate was added to the solution and the inner temperature was adjusted to 20° C., 5 ml of the 1,2-dichloroethane solution containing ethyl diazoacetate (concentration: 4 mol/l) was added dropwise thereto over 4 hours and the resulting mixture was reacted at the same temperature for 30 minutes to obtain the solution containing ethyl 3,3-dimethyl-2-(acetoxymethyl)cyclopropanecarboxylate.
Yield: 56%
Trans-isomer/cis-isomer ratio: 81/19
Optically purity: trans-isomer 93% e.e. ((+)-isomer), cis-isomer 40% e.e. ((+)-isomer)

Example 4

Into a 50 ml Schlenk tube purged with nitrogen, 1.98 mg of copper(I) chloride, 6.43 mg of 1,1-bis[2-[(4S)-(tert-butyl)oxazoline]]cyclopropane and 5 ml of 1,2-dichloroethane were charged. To the pale yellow mixture obtained by mixing them, 8.54 mg of trityl hexafluorophosphate was added and the resulting mixture was stirred at room temperature for 10 minutes to obtain the lime green solution containing the asymmetric copper complex. The solution was analyzed by gas chromatography to confirm the production of trityl chloride. After 7.69 g of 3-methyl-2-butenyl acetate was added to the solution and the inner temperature was adjusted to 20° C., 5 ml of the 1,2-dichloroethane solution containing ethyl diazoacetate (concentration: 4 mol/l) was added dropwise thereto over 4 hours and the resulting mixture was reacted at the same temperature for 30 minutes to obtain the solution containing ethyl 3,3-dimethyl-2-(acetoxymethyl)cyclopropanecarboxylate.
Yield: 69%
Trans-isomer/cis-isomer ratio: 84/16
Optically purity: trans-isomer 92% e.e. ((+)-isomer), cis-isomer 46% e.e. ((+)-isomer)

Comparative Example 1

Into a 50 ml Schlenk tube purged with nitrogen, 5.17 mg of copper(I) trifluoromethanesulfonate toluene complex, 6.43 mg of 1,1-bis[2-[(4S)-(tert-butyl)oxazoline]]cyclopropane and 5 ml of 1,2-dichloroethane were charged and the resulting mixture was stirred at room temperature for 10 minutes to obtain the yellow homogeneous solution containing the asymmetric copper complex. After 7.69 g of 3-methyl-2-butenyl acetate was added to the homogeneous solution and the inner temperature was adjusted to 20° C., 5 ml of the 1,2-dichloroethane solution containing ethyl diazoacetate (concentration: 4 mol/l) was added dropwise thereto over 4 hours and the resulting mixture was reacted at the same temperature for 30 minutes to obtain the solution containing ethyl 3,3-dimethyl-2-(acetoxymethyl)cyclopropanecarboxylate.
Yield: 58%
Trans-isomer/cis-isomer ratio: 81/19
Optically purity: trans-isomer 92% e.e. ((+)-isomer), cis-isomer 65% e.e. ((+)-isomer)

Example 5

According to the same manner as that described in Example 4, the solution containing ethyl 3,3-dimethyl-2-(benzyloxymethyl)cyclopropanecarboxylate was obtained except that 7.05 g of (3-methyl-2-butenyl)benzyl ether was used in place of 7.69 g of 3-methyl-2-butenyl acetate.
Yield: 75%
Trans-isomer/cis-isomer ratio: 88/12
Optically purity: trans-isomer 92% e.e. ((+)-isomer), cis-isomer 3% e.e. ((−)-isomer)

Comparative Example 2

According to the same manner as that described in Comparative Example 1, the solution containing ethyl 3,3-dimethyl-2-(benzyloxymethyl)cyclopropanecarboxylate was obtained except that 7.08 g of (3-methyl-2-butenyl)benzyl ether was used in place of 7.69 g of 3-methyl-2-butenyl acetate.
Yield: 71%
Trans-isomer/cis-isomer ratio: 84/16
Optically purity: trans-isomer 88% e.e. ((+)-isomer), cis-isomer 52% e.e. ((−)-isomer)

Example 6

Into a 50 ml Schlenk tube purged with nitrogen, 2.48 mg of copper(I) chloride, 13.49 mg of 2,2-bis[2-[(4S)-(1-naphthyl)-5,5-dimethyloxazoline]]propane and 5 ml of 1,2-dichloroethane were charged. To the pale yellow mixture obtained by mixing them, 10.68 mg of trityl hexafluorophosphate was added and the resulting mixture was stirred at room temperature for 10 minutes to obtain the lime green solution containing the asymmetric copper complex. After 3.9 g of 2,5-dimethyl-2,4-hexadiene was added to the solution and the inner temperature was adjusted to 0° C., 5 ml of the 1,2-dichloroethane solution containing tert-butyl diazoacetate (concentration: 1 mol/l) was added dropwise thereto over 3 hours and the resulting mixture was reacted at the same temperature for 30 minutes to obtain the solution containing tert-butyl 2,2-dimethyl-3-(2-methyl-1-propenyl)cyclopropanecarboxylate.
Yield: 91%
Trans-isomer/cis-isomer ratio: 88/12
Optically purity: trans-isomer 96% e.e. ((+)-isomer), cis-isomer 71% e.e. ((+)-isomer)

Example 7

According to the same manner as that described in Example 6, the solution containing tert-butyl 2,2-dimethyl-3-(2-methyl-1-propenyl)cyclopropanecarboxylate was obtained except that 9.45 mg of silver hexafluoroantimonate was used in place of 10.68 mg of trityl hexafluorophosphate.
Yield: 88%
Trans-isomer/cis-isomer ratio: 88/12
Optically purity: trans-isomer 94% e.e. ((+)-isomer), cis-isomer 73% e.e. ((−)-isomer)

Comparative Example 3

Into a 50 ml Schlenk tube purged with nitrogen, 6.47 mg of copper(I) trifluoromethanesulfonate toluene complex and 5 ml of dichloroethane were charged. To the white suspension obtained by mixing them, 13.49 mg of 2,2-bis[2-[(4S)-(1-naphthyl)-5,5-dimethyloxazoline]]propane was added and the resulting mixture was stirred at room temperature for 10 minutes to obtain the blue homogeneous solution containing the asymmetric copper complex. After 3.9 g of 2,5-dimethyl-2,4-hexadiene was added to the homogeneous solution and the inner temperature was adjusted to 0° C., 5 ml of the 1,2-dichloroethane solution containing tert-butyl diazoacetate (concentration: 1 mol/l) was added dropwise thereto over 3 hours and the resulting mixture was reacted at the same temperature for 30 minutes to obtain the solution containing tert-butyl 2,2-dimethyl-3-(2-methyl-1-propenyl)cyclopropanecarboxylate.
Yield: 83%
Trans-isomer/cis-isomer ratio: 87/13
Optically purity: trans-isomer 96% e.e. ((+)-isomer), cis-isomer 71% e.e. ((−)-isomer)

INDUSTRIAL APPLICABILITY

According to the present invention, it is possible to produce an optically active cyclopropanecarboxylate compound which is useful as a synthetic intermediate of pesticides and pharmaceuticals such as synthesized pyrethroid insecticides.

The invention claimed is:
1. A method for producing an optically active cyclopropanecarboxylate compound represented by the formula (5):

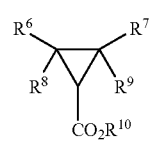

(5)

wherein $R^6$, $R^7$, $R^8$ and $R^9$ are the same or different, and independently represent a hydrogen atom; a halogen atom; a C1-C6 alkyl group which is optionally substituted with a halogen atom or atoms, a C1-C6 alkoxy group or groups, a C7-C12 aralkyloxy group or groups, a C2-C10 acyloxy group or groups, a C2-C7 alkoxycarbonyloxy group or groups, or a C7-C11 aryloxycarbonyloxy group or groups; a C1-C6 alkenyl group which is optionally substituted with a halogen atom or atoms or a C2-C7 alkoxycarbonyl group or groups; a C6-C10 aryl group which is optionally substituted with a C1-C6 alkoxy group or groups; a C7-C12 aralkyl group which is optionally substituted with a C1-C6 alkoxy group or groups; or a C2-C7 alkoxycarbonyl group which is optionally substituted with a halogen atom or atoms, a C1-C6 alkoxy group or groups, a C7-C12 aralkyloxy group or groups, a C2-C10 acyloxy group or groups, a C2-C7 alkoxycarbonyloxy group or groups, or a C7-C11 aryloxycarbonyloxy group or groups; provided that, when $R^6$ and $R^8$ represent the same, $R^6$ and $R^7$ represent different groups each other; and $R^{10}$ represents a C1-C6 alkyl group, which comprises reacting an olefin represented by the formula (3):

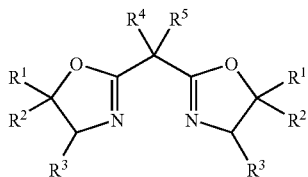

(3)

wherein $R^6$, $R^7$, $R^8$ and $R^9$ are as described above, with a diazoacetic acid ester represented by the formula (4):

$$N_2CHCO_2R^{10} \qquad (4)$$

wherein $R^{10}$ is as described above, in the presence of an asymmetric copper complex obtained by mixing (A) at least one monovalent or divalent copper compound, (B) at least one optically active bisoxazoline compound represented by the formula (1):

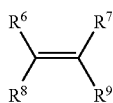

(1)

wherein $R^1$ and $R^2$ are the same or different, and independently represent a hydrogen atom; a C1-C6 alkyl group; a phenyl group which is optionally substituted with a C1-C6 alkyl group or groups, or a C1-C6 alkoxy group or groups; or a C7-C12 aralkyl group which is optionally substituted with a C1-C6 alkoxy group or groups, or $R^1$ and $R^2$ are bonded together to represent a C2-C6 polymethylene group, $R^3$ represents a methyl group; an isopropyl group; an isobutyl group; a tert-butyl group; a 1-naphthyl group; a 2-naphthyl group; a phenyl group which is optionally substituted with a C1-C6 alkyl group or groups, or a C1-C6 alkoxy group or groups; or a C7-C12 aralkyl group which is optionally substituted with a C1-C6 alkoxy group or groups, and $R^4$ and $R^5$ are the same and represent hydrogen atoms or C1-C3 alkyl groups, or $R^4$ and $R^5$ are bonded together to represent a C2-C5 polymethylene group, and (C) at least one fluorine compound represented by the formula (2):

$$A\text{-}MF_6 \qquad (2)$$

wherein A represents a lithium atom, a sodium atom, a potassium atom, a silver atom or a trityl group, and M represents a phosphorous, arsenic or antimony atom.

2. The method according to claim 1, wherein the component (A) is at least one monovalent copper compound.

3. The method according to claim 1, wherein the copper compound is a copper halide in the component (A).

4. The method according to claim 1, wherein A is a trityl group in the component (C).

5. The method according to claim 1, wherein in the formula (3), (a) $R^6$ and $R^8$ are methyl groups, $R^7$ is a hydrogen atom; a C1-C6 alkyl group substituted with a C7-C12 aralkyloxy group or groups, or a C2-C10 acyloxy group or groups; or a C1-C6 alkenyl group which is optionally substituted with a halogen atom or atoms, and $R^9$ is a hydrogen atom or (b) $R^6$ and $R^8$ are hydrogen atoms, $R^7$ is an aryl group which is optionally substituted with a C1-C6 alkoxy group or groups; or a halogen atom, and $R^9$ is a hydrogen or halogen atom.

6. The method according to claim 1, wherein in the formula (3), (a) $R^6$ and $R^8$ are methyl groups, $R^7$ is a hydrogen atom, a benzyloxymethyl group, an acetoxymethyl group, a 2-methyl-1-propenyl group, a 2,2-dichloroethenyl group, a 2,2dibromoethenyl group or 2-chloro-2-fluoroethenyl group, and $R^9$ is a hydrogen atom or (b) $R^6$ and $R^8$ are hydrogen atoms, $R^7$ is a 2,3-dihydrobenzofuran-4-yl group or a fluorine atom, and $R^9$ is a hydrogen or fluorine atom.

7. An asymmetric copper complex obtained by mixing the components (A) at least one monovalent or divalent copper compound, (B) at least one optically active bisoxazoline compound represented by the formula (1):

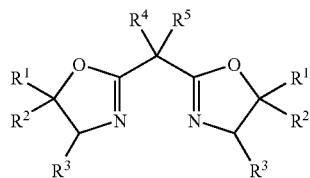

(1)

wherein $R^1$ and $R^2$ are the same or different, and independently represent a hydrogen atom; a C1-C6 alkyl group; a phenyl group which is optionally substituted with a C1-C6 alkyl group or groups, or a C1-C6 alkoxy group or groups; or a C7-C12 aralkyl group which is optionally substituted with a C1-C6 alkoxy group or groups, or $R^1$ and $R^2$ are bonded together to represent a C2-C6 polymethylene group, $R^3$ represents a methyl group; an isopropyl group; an isobutyl group; a tert-butyl group; a 1-naphthyl group; a 2-naphthyl group; a phenyl group which is optionally substituted with a C1-C6 alkyl group or groups, or a C1-C6 alkoxy group or groups; or a C7-C12 aralkyl group which is optionally substituted with a C1-C6 alkoxy group or groups, and $R^4$ and $R^5$ are the same and represent hydrogen atoms or C1-C3 alkyl groups, or $R^4$ and $R^5$ are bonded together to represent a C2-C5 polymethylene group, and (C) at least one fluorine compound represented by the formula (2):

$$A\text{-}MF_6 \qquad (2)$$

wherein A represents a lithium atom, a sodium atom, a potassium atom, a silver atom or a trityl group, and M represents a phosphorous, arsenic or antimony atom.

8. The asymmetric copper complex according to claim 7, wherein the component (A) is at least one monovalent copper compound.

9. The asymmetric copper complex according to claim 7, wherein the copper compound is a copper halide in the component (A).

10. The asymmetric copper complex according to claim 7, wherein A is the trityl group in the component (C).

* * * * *